(12) United States Patent
    Todd et al.

(10) Patent No.: US 12,640,242 B1
(45) Date of Patent: *May 26, 2026

(54) MEMBER-SPECIFIC FORMULARY DATA INTERFACE OVERLAY

(71) Applicant: Xact Laboratories, LLC, Twinsburg, OH (US)

(72) Inventors: Rob Todd, Doylestown, PA (US); Jerry Wrobel, Aurora, OH (US); John Pigott, Slyvania, OH (US); Cassandra Talafous, North Lawrence, OH (US)

(73) Assignee: Xact Laboratories, LLC, Twinsburg, OH (US)

( * ) Notice: Subject to any disclaimer, the term of this patent is extended or adjusted under 35 U.S.C. 154(b) by 562 days.

This patent is subject to a terminal disclaimer.

(21) Appl. No.: 17/675,885

(22) Filed: Feb. 18, 2022

(51) Int. Cl.
| | |
|---|---|
| *G16H 10/60* | (2018.01) |
| *G16H 15/00* | (2018.01) |
| *G16H 20/10* | (2018.01) |
| *G16H 40/67* | (2018.01) |

(52) U.S. Cl.
    CPC ............. *G16H 10/60* (2018.01); *G16H 15/00* (2018.01); *G16H 20/10* (2018.01); *G16H 40/67* (2018.01)

(58) Field of Classification Search
    CPC ........ G16H 10/60; G16H 15/00; G16H 20/10; G16H 40/67
    USPC ........................................................ 705/2–3
    See application file for complete search history.

(56) References Cited

U.S. PATENT DOCUMENTS

| | | | |
|---|---|---|---|
| 6,315,720 | B1 | 11/2001 | Williams et al. |
| 8,386,274 | B1 | 2/2013 | Pinsonneault |
| 10,950,354 | B1 | 3/2021 | Belgoroski |
| 11,281,194 | B1 * | 3/2022 | Fernando ......... G05B 19/41865 |
| 11,527,331 | B2 * | 12/2022 | Todd ...................... G16B 20/00 |
| 11,626,191 | B1 | 4/2023 | Gartner |
| 2002/0012921 | A1 | 1/2002 | Stanton, Jr. |
| 2002/0052761 | A1 | 5/2002 | Fey et al. |
| 2002/0115073 | A1 | 8/2002 | Papadopoulos et al. |
| 2002/0147616 | A1 | 10/2002 | Pollard et al. |
| 2002/0187483 | A1 | 12/2002 | Hoffman et al. |

(Continued)

FOREIGN PATENT DOCUMENTS

WO        2013096729 A2      6/2013

OTHER PUBLICATIONS

Wikipedia, Formulary (pharmacy), retrieved Feb. 27, 2025, https://en.wikipedia.org/wiki/Formulary_(pharmacy) (Year: 2025).*

(Continued)

*Primary Examiner* — Kambiz Abdi
*Assistant Examiner* — Tran N Nguyen
(74) *Attorney, Agent, or Firm* — Standley Law Group LLP; Adam J. Smith; Jeffrey S. Standley

(57)        ABSTRACT

An electronic data interface overlay for modifying existing formulary data is provided along with systems and methods for the same. The overlay comprises member-specific clinical data and causes automatic generation of code(s) indicating coverage denial upon querying of treatments of the existing formulary data associated with certain of the member-specific clinical data, such as pharmacogenetic ("PGx") test results, of the data interface overlay. The formulary data includes alternative treatments which may be suggested and approved upon denial based on PGx test results. An electronic health record is automatically updated with the alternative treatment.

17 Claims, 11 Drawing Sheets

(56) References Cited

U.S. PATENT DOCUMENTS

| | | | |
|---|---|---|---|
| 2003/0040002 A1 | 2/2003 | Ledley | |
| 2003/0046110 A1 | 3/2003 | Gogolak | |
| 2003/0073124 A1 | 4/2003 | Bowman et al. | |
| 2004/0153662 A1* | 8/2004 | Rumpel | G16H 50/20 |
| | | | 726/27 |
| 2005/0026117 A1 | 2/2005 | Judson et al. | |
| 2005/0107672 A1 | 5/2005 | Lipscher et al. | |
| 2005/0149361 A1 | 7/2005 | Saus et al. | |
| 2006/0010009 A1* | 1/2006 | Fangman | G16H 70/40 |
| | | | 705/2 |
| 2006/0178843 A1 | 8/2006 | Athanasiou | |
| 2006/0259325 A1 | 11/2006 | Patterson | |
| 2007/0178501 A1 | 8/2007 | Rabinowitz et al. | |
| 2008/0015893 A1* | 1/2008 | Miller | G16H 70/40 |
| | | | 600/300 |
| 2008/0091464 A1 | 4/2008 | Lipscher et al. | |
| 2008/0131887 A1 | 6/2008 | Stephan et al. | |
| 2008/0162352 A1 | 7/2008 | Gizewski | |
| 2008/0228824 A1 | 9/2008 | Kenedy | |
| 2009/0094059 A1 | 4/2009 | Coleman et al. | |
| 2009/0198519 A1 | 8/2009 | McNamar | |
| 2009/0240523 A1 | 9/2009 | Friedlander et al. | |
| 2010/0070455 A1 | 3/2010 | Halperin et al. | |
| 2010/0317006 A1 | 12/2010 | Soykan et al. | |
| 2011/0113002 A1* | 5/2011 | Kane | G16B 20/00 |
| | | | 706/50 |
| 2012/0010903 A9* | 1/2012 | Gaziano | G16H 10/20 |
| | | | 705/3 |
| 2012/0065999 A1 | 3/2012 | Takatoku et al. | |
| 2012/0185270 A1 | 7/2012 | Scantland et al. | |
| 2013/0096943 A1 | 4/2013 | Carey et al. | |
| 2013/0226621 A1 | 8/2013 | Van Der Zaag | |
| 2013/0246079 A1 | 9/2013 | Hoffman et al. | |
| 2014/0012843 A1 | 1/2014 | Soon-Shiong | |
| 2014/0211204 A1 | 7/2014 | Stedtfeld | |
| 2014/0244309 A1 | 8/2014 | Francois | |
| 2014/0303992 A1 | 10/2014 | Scantland et al. | |
| 2014/0316821 A1 | 10/2014 | Sheffield et al. | |
| 2014/0350954 A1 | 11/2014 | Ellis et al. | |
| 2014/0372141 A1 | 12/2014 | Renner et al. | |
| 2015/0058030 A1 | 2/2015 | Scantland et al. | |
| 2015/0058039 A1* | 2/2015 | Shiloh | G06F 16/24 |
| | | | 705/3 |
| 2015/0170291 A1 | 6/2015 | Renner et al. | |
| 2015/0228030 A1 | 8/2015 | Scantland et al. | |
| 2016/0048652 A1 | 2/2016 | Spivey et al. | |
| 2016/0092652 A1 | 3/2016 | Stewart et al. | |
| 2016/0180063 A1 | 6/2016 | Scantland et al. | |
| 2016/0239636 A1 | 8/2016 | O'Donnell et al. | |
| 2017/0004282 A1 | 1/2017 | Scantland et al. | |
| 2017/0046491 A1 | 2/2017 | Scantland et al. | |
| 2017/0046492 A1 | 2/2017 | Renner et al. | |
| 2017/0124254 A1 | 5/2017 | van Rooyen | |
| 2017/0213011 A1 | 7/2017 | Hoffman et al. | |
| 2017/0270246 A1 | 9/2017 | Baskys | |
| 2017/0293722 A1 | 10/2017 | Valverde, Jr. | |
| 2017/0308669 A1 | 10/2017 | Apte et al. | |
| 2018/0075220 A1 | 3/2018 | Hill, Sr. et al. | |
| 2018/0308569 A1 | 10/2018 | Luellen | |
| 2018/0330060 A1 | 11/2018 | Biles et al. | |
| 2018/0330824 A1 | 11/2018 | Athey | |
| 2019/0244688 A1 | 8/2019 | Wilson et al. | |
| 2020/0005921 A1 | 1/2020 | Hill, Sr. et al. | |
| 2020/0135314 A1* | 4/2020 | Gostyla | G16H 15/00 |
| 2020/0160958 A1 | 5/2020 | Huser | |
| 2020/0365280 A1* | 11/2020 | Todd | G16H 40/20 |
| 2021/0065861 A1* | 3/2021 | Lamoncha | G16H 20/10 |
| 2021/0319871 A1 | 10/2021 | Hanz | |

OTHER PUBLICATIONS

Translational Software, Insights Ready for Action archived webpage, https://web.archive.org/web/20180829020620/https://translationalsoftware.com/, Aug. 29, 2018, 9 pages.

Clinisync, Clinisync Products and Services webpage, http://www.clinisync.org/, Jul. 18, 2018, 5 pages.

Althoff, Lisa, DNA Chip—Genetic Testing of the Future webpage, https://www.ndsu.edu/pubweb/~mcclean/plsc431/students99/althoff.html, Copyright 1999, Aug. 2, 2019, 5 pages.

LabX, DNA Sequencers Listings webpage, https://www.labx.com/dna-sequencers, Aug. 2, 2019, 3 pages.

Vecna, Vecna Patient Solutions webpage, https://healthcare.vecna.com/, Jul. 18, 2019, 11 pages.

Translational Software, Making Sense of Pharmacogenomics Testing webpage, https://translationalsoftware.com/, Sep. 11, 2019, 14 pages.

Translational Software, Integrated Into Clinical Systems archived webpage, https://web.archive.org/web/20171217010330/https://translationalsoftware.com/, Oct. 17, 2017, 7 pages.

Translational Software, Insights Ready for Action archived webpage, https://web.archive.org/web/20180829020620/https://translationalsoftwarre.com/, Aug. 29, 2018, 9 pages.

Coriell Life Sciences, GeneDose—Medication Risk Management Tool archived webpage, https://web.archive.org/web/20170611205541/http://genedose.com/, Jun. 11, 2017, 8 pages.

Coriell Life Sciences, DNA-Driven Diagnostics to Guide Clinical Decision-Making webpage, https://www.coriell.com/genetic-interpretation-reporting/, Sep. 11, 2019, 9 pages.

Coriell Life Services, GeneDose Youtube Video, https://youtube.com/watch?v=tku6_9tADuw, Sep. 11, 2019.

Caraballo et al., Electronic Medical Record-Integrated Pharmacogenomics and Related Clinical Decision Support Concepts, Aug. 2017, Clinical Pharmacology & Therapeutics, vol. 102 No. 2, pp. 254-264.

Hicks, J. Kevin, et al., Integrating Pharmacogenomics into Electronic Health Records with Clinical Decision Support, Am J Health Syst. Pharm. Author Manuscript, Dec. 1, 2016, 17 pgs., HHS Public Access.

Hinderer, Marc, et al., Integrating Clinical Decision Support for Pharmacogenomic Testing into Clinical Routine—a Scoping Review of Designs of User-System Interactions in Recent System Development, Research Article, Jun. 6, 2017, 14 pgs., BioMed Central.

Jensen, Peter, et al., Mining Electronic Health Records: Towards Better Research Applications and Clinical Care, Translational Genetics, Nature Reviews: Genetics, vol. 13, Jun. 2012, pp. 395-405.

Peterson et al., Electronic Health Record Design and Implementation for Pharmacogenomics: a local perspective, Oct. 2013, Genetics in Medicine, vol. 15 No. 10.

Naples, Eric C., What Does CMS' Real-Time Benefit Tool Final Rule Mean for the Healthcare Industry?, Blog, Jan. 22, 2020, 7 pgs., RxRevu, Inc.

Covermymeds, RxBenefit Clarity: Empowering Providers and Their Patients with Prescription Price Transparency, Feb. 9, 2022, 13 pgs.

Surescripts, Real-Time Benefit Check: Enhancing Provider and Patient Choice from Within the EHR, 2 pgs.

AVS Medical, NextGen Office Adds ChangeRX and Cancel RX to Their Cloud Based EHR, AVS-Blog, Mar. 1, 2019, 1 pg.

DrFirst, DrFirst Launches myBenefitCheck Real-Time Benefit Check Capabilities to Help Patients Better Manage Medication Costs and Adherence DrFirst, Press Release, Oct. 22, 2015, 5 pgs., DrFirst Healthcare Innovations, Canada.

Sutter Community Connect, Cancel Rx and Change Rx, Tip Sheet, AMB Clinicians, Dec. 10, 2019, 7 pgs.

Mccain, Lauren Ann, A Policy Appraisal of the United States Human Genome Project, Order No. 3096828, University of Colorado at Boulder, 2003.

* cited by examiner

20

10

308

Definition of Status

| Status | Definition |
|---|---|
| Generic | Generic. Your cost-share will depend on your enrollment option |
| Preferred Brand | Preferred Brand. Your cost-share will depend on your enrollment option |
| Non-Preferred Drug | Non-Preferred Drug. Your cost-share will depend on your enrollment option. |
| S8 HCR | Coverage for certain products is available at no-cost share with a doctor's prescription when provided by a participating retail or mail-order pharmacy and as described in the Patient Protection and Affordable Care Act (PPACA) and detailed by the U.S. Preventive Services Task Force or mandated by the Women's Preventive Services provision. Coverage outside of these guidelines are determined by the member's benefits. |
| Medical Benefit | Drug is covered under the plan's medical benefit and is excluded from coverage under the plan's pharmacy benefit. For more information on medications covered under the medical benefit, please refer to the plan's website. |
| Excluded Drug | Excluded Drug |

Definition of Restrictions

| Restriction | Definition |
|---|---|
| Additional Limits Apply | Please read |
| Age Restriction | Age Restriction - Certain medications may not be age appropriate for all members. An age edit may be placed on a medication when safety concerns or inappropriate issues exist for a particular age group |
| Authorized Generic | The term "authorized generic" drug is most commonly used to describe an approved brand name drug that is marketed without the brand name on its label. Other than the fact that it does not have the brand name on its label, it is the exact same drug product as the branded product. Unlike a standard generic drug, the Authorized Generic is not approved by the Food and Drug Administration (FDA) as a generic drug. Accordingly, for cost sharing purposes Authorized generics are treated as brand name drugs. |
| Generic Indicator | Generic Indicator |
| HSA-qualified HDHP | Please read |
| Important Information | Please read |
| Important Information | Please read |
| Maintenance Medication | Maintenance Medication |
| Over The Counter | Over The Counter |
| Prior Authorization | We require you or your physician to get prior authorization for certain drugs. This means that you will need to get approval from us before you fill your prescriptions. If you don't get approval, we may not cover the drug. Click on the PA icon for the link to the prior authorization form |
| Quantity Limit | For certain drugs, we limit the amount of the drug that we will cover. Click on this symbol next to the drug for more information. |
| Specialty Pharmacy | Denotes medication is considered a specialty drug as defined by your benefit. Access may be limited to the preferred Specialty Pharmacy. |

MEMBER-SPECIFIC FORMULARY DATA INTERFACE OVERLAY

CROSS-REFERENCE TO RELATED APPLICATION

This application makes no priority claim.

TECHNICAL FIELD

Exemplary embodiments relate generally to systems and methods for providing formulary data interface overlays for clinical data, such as on a member-specific basis to reflect pharmacogenomic ("PGx") efficacy testing results.

BACKGROUND AND SUMMARY OF THE INVENTION

Health plan providers have an interest in avoiding unnecessary expenses, which may otherwise translate to increased premium costs, which are generally passed along to covered individuals. One example of an unnecessary expense may be payment for ineffective or undereffective treatments, particularly when an alternative which may be fully or more effective is available. PGx efficacy testing is one way health plan providers may avoid or limit unnecessary expenses.

Members have an interest in avoiding unnecessary treatments, which may otherwise cause unnecessary expense and exposure to side effects. One example of an unnecessary treatment may be ineffective or undereffective medications, particularly when an alternative which may be fully or more effective is available. PGx efficacy testing is one way that members may avoid or limit unnecessary treatments.

What is needed is a system for alerting interested parties, such as health plan providers and/or members, to clinical data and/or available PGx efficacy testing.

Systems and methods are provided herein for integrating clinical information, such as, but not limited to, PGx efficacy testing results and/or available PGx efficacy testing indications, with a health plan. Such results may be integrated into a formulary, in exemplary embodiments without limitation. As used herein, PGx efficacy testing, PGx testing, or the like may refer to genetic testing performed to understand treatment efficacy, such as, but not limited to, administration of medications, based on a person's genetic makeup. Such PGx testing may be of a select portion or portions of a person's DNA, or of an entire DNA sequence.

Health plans may identify members for which PGx testing is desirable. Such identification may be made on the basis of various criteria, which may be defined by the health plan in exemplary embodiments. Such reviews may be triggered on an on-demand basis, performed periodically, occasionally, and/or randomly, upon addition of new members, upon update to formulary information, upon update to available PGx testing information, upon update to PGx efficacy information, combinations thereof, or the like.

Health plans may reach out to identified members for consent to testing. In exemplary embodiments, without limitation, testing kits may be assembled and mailed to identified and/or consenting members in an at least partially automated fashion. Members may provide specimens to a laboratory for testing, such as by following instructions in a testing kit. Specimens received from the members may be processed through ordered testing by a laboratory. In exemplary embodiments, without limitation, testing may be performed in an at least partially automated fashion.

Test results may be reported by a laboratory information system ("LIS") of the laboratory to the health plan, such as for generation of exclusion criteria. In exemplary embodiments, without limitation, the LIS may generate the exclusion criteria based on the test results. Alternatively, or additionally, the testing results and/or exclusion criteria may be provided in the form of one or more data interface overlays (hereinafter also the "overlay" or "overlays") for the formulary, which may be administered by a pharmacy benefits manager ("PBM") system in exemplary embodiments. In this manner, member-specific information, versions, or sections of the formulary may be generated based on individual member results.

Testing may be provided at a fixed rate between the health plan and the laboratory, such that zero costs is provided directly to a tested member by way of non-limiting example. The return on investment for a health plan and member may be avoiding unnecessary expenses and treatment to avoid increased premium costs, which are generally passed along to covered individuals. Members may be incentive for testing to avoid unnecessary treatments, receive one or more discounts or other benefits, as a requirement for continued coverage of prescription medication refills, to understand their own genetic makeup, combinations thereof, or the like. By integrating with the formulary, the clinical information, such as, but not limited to, exclusion criteria and/or PGx test results, may be member-specific and/or may be portable across different PBM providers.

The overlay modified formulary may be configured to provide automated triggering of prescription (hereinafter also "Rx") coverage approvals or denials upon receipt of Rx coverage requests. These coverage approvals or denials may be made on a member-specific basis, such as based on a member-specific formulary and/or information, and in accordance with the PGx testing results and/or other clinical information integrated with the formulary by the overlay(s). The overlay(s) may be generated by the LIS and electronically transmitted to the health plan and/or PBM system, directly or indirectly, for integration with the formulary, though such is not required.

Alternatively, or additionally, the same or different overlay(s) may be used to identify treatments within the formulary for which PGx testing is available. Such overlay(s) may be generated by the LIS, though such is not required. When applied to the formulary, such overlay(s) may be configured to automatically identify medication for which PGx efficacy testing is available. Such members may be identified upon review of member data, and available PGx testing may be one of the criteria. Alternatively, or additionally, upon coverage request for medications indicated within the formulary as being associated with available PGx testing, coverage may be denied until such testing is performed. Alternatively, or additionally, a single or limited supply of medication may be approved for coverage and completion of PGx testing and may be required for continued coverage. Alternatively, or additionally, alternative treatment options may be sought in existing formulary data for non-PGx testing dependent, but otherwise covered, alternative treatment options.

For example, without limitation, when modified with the overlay(s) and upon query of a treatment option with which PGx testing is available but no test results are stored, the overlay(s) may configure the PBM system to automatically generate one or more codes reflecting the available testing, denying coverage, and/or providing temporary coverage on a limited basis until such testing is performed. The PBM system may, alternatively or additionally, be configured to notify the LIS of the same, which may trigger the LIS to perform one or more of: a proposed order generation, member specimen collection kit generation, consent obtainment, combinations thereof, or the like. The processes and systems for undertaking the same may be as shown and/or described herein.

Where a coverage denial is initially received, such as based on PGx results, a modification request may be made, such as through a modification/cancellation platform. Such modification requests may be performed where alternative treatment options are available in exemplary embodiments. For example, without limitation, the formulary may be queried for alternative treatment options. If one or more alternatives are available, such as defined by the formulary, an electronic notification may be transmitted to the healthcare provider's office, such as by way of an EHR system associated with the healthcare provider and/or their office and/or the modification/cancellation platform, for approval/denial of the one or more alternatives. If approved, the alternative treatment(s) may be filled by the pharmacy. Furthermore, the EHR system may be automatically updated to reflect prescription of the alternative treatment(s) in lieu of the originally prescribed, and denied, treatment. Such updating may be performed by way of the modification/cancellation platform.

Other EHR systems associated with other healthcare providers or offices associated with the member may be updated automatically, such as by way of one or more healthcare information exchange ("HIE") systems.

In accordance with the formulary, such as when modified by the overlay(s), the PBM system may be configured to automatically generate one or more PGx specific codes when coverage is denied based on PGx results, or a lack of PGx testing results. The PGx specific codes may be transmitted to the requesting pharmacy system and/or health care provider EHR system. The PGx specific codes may comprise one or more National Council for Prescription Drug Programs ("NCPDP") codes (www.ncpdp.org/), though such is not required.

The aforementioned disclosures may permit member specific PGx data, and/or other clinical data, to be utilized by health plans for integration with an existing formulary to provide member-specific alerting. In this manner, the clinical data may be used by a health plan independent of PBM provider, pharmacy, or the like that are utilized, permitting portability. This may alternatively, or additionally, permit alerts to be automatically generated, such as for available PGx testing and/or ineffective treatments based on a member-specific basis. While PGx testing availability and results are discussed, other clinical information may alternatively, or additionally, be integrated into the formulary in this fashion.

PGx testing results may optionally be reported to other interested parties, including, but not limited to, the pharmacy, healthcare provider, other healthcare providers associated with the member, other payors associated with the member, the member, caretakers, other authorized parties, combinations thereof, or the like. Such reporting may be performed by the LIS, directly or indirectly, such as on a courtesy basis, though such is not required.

Further features and advantages of the devices and systems disclosed herein, as well as the structure and operation of various aspects of the present disclosure, are described in detail below with reference to the accompanying figures.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein:

FIG. 12 is an exemplary indicators legend for the medication reports of FIGS. 9A, 10A, and 11.

DETAILED DESCRIPTION OF EXEMPLARY EMBODIMENT(S)

Various embodiments of the present invention will now be described in detail with reference to the accompanying drawings. In the following description, specific details such as detailed configuration and components are merely provided to assist the overall understanding of these embodiments of the present invention. Therefore, it should be apparent to those skilled in the art that various changes and modifications of the embodiments described herein can be made without departing from the scope and spirit of the present invention. In addition, descriptions of well-known functions and constructions are omitted for clarity and conciseness.

Figure 1B:
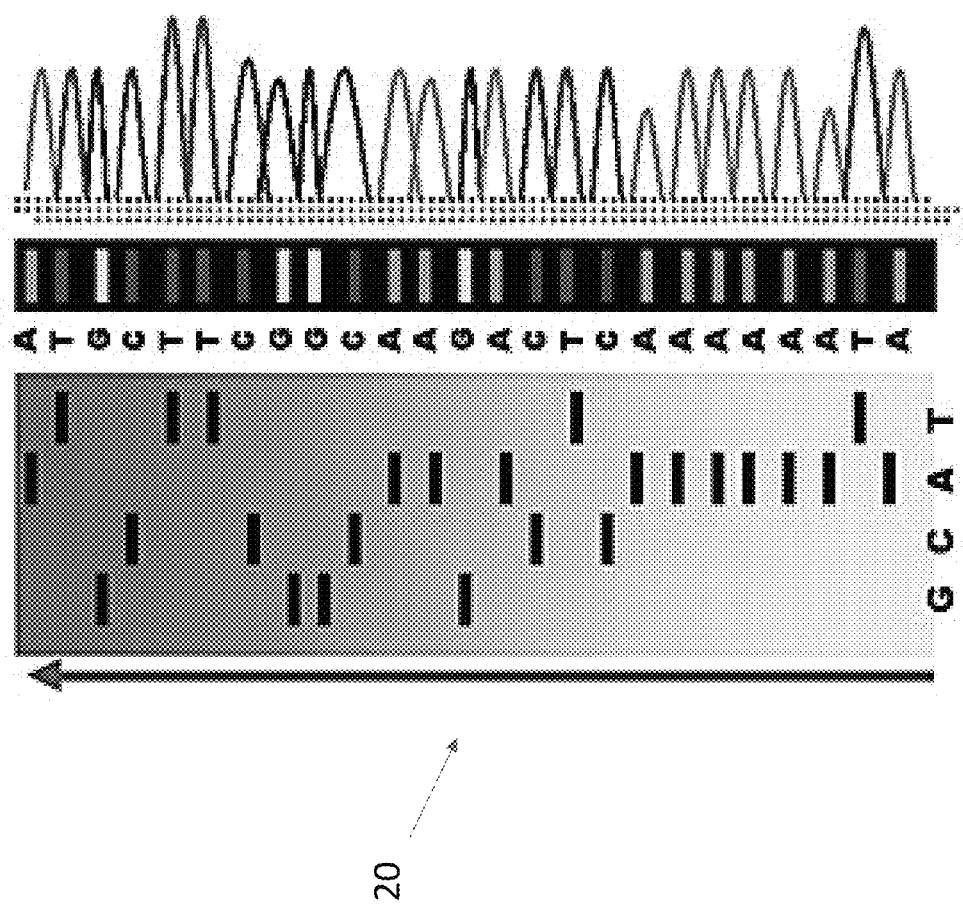
FIG. 1B is a simplified illustration of a DNA sequencing test result.
Figure 1A:
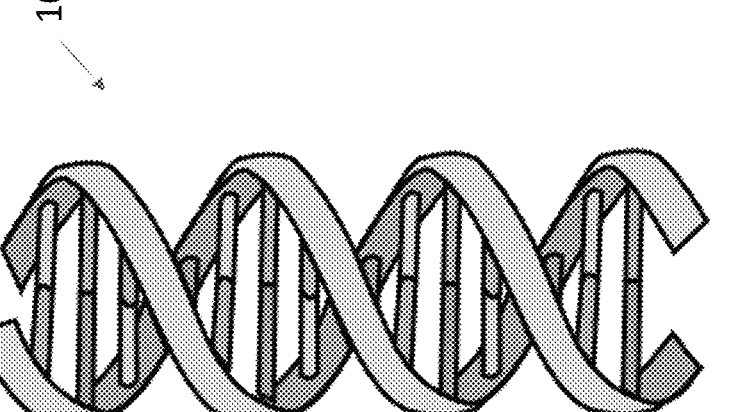
FIG. 1A is a simplified illustration of a DNA helix.

FIG. 1A is a simplified illustration of a DNA helix 10. DNA, or deoxyribonucleic acid, is a double-helix shaped chain of nucleotides that carry the genetic instructions used in the growth, development, functioning, and reproduction of all known living organisms. There are four major types of nucleobases in any nucleotide of a DNA sequence, which are generally coded as A, T, C, and G for adenine, thymine, cytosine, and guanine, respectively. Each individual human is believed to have a unique DNA structure that defines the person's genetic makeup.

FIG. 1B is a simplified illustration of a DNA sequencing test result 20. Upon sequencing of the DNA 10, the presence or non-presence of particular nucleobases (A, T, C, or G) may be detected. The presence and non-presence or order of such nucleobases can be used to determine the presence or non-presence of certain genetic markers. The genetic markers may indicate the existence or non-existence of certain genetic traits for the person.

Figure 2:
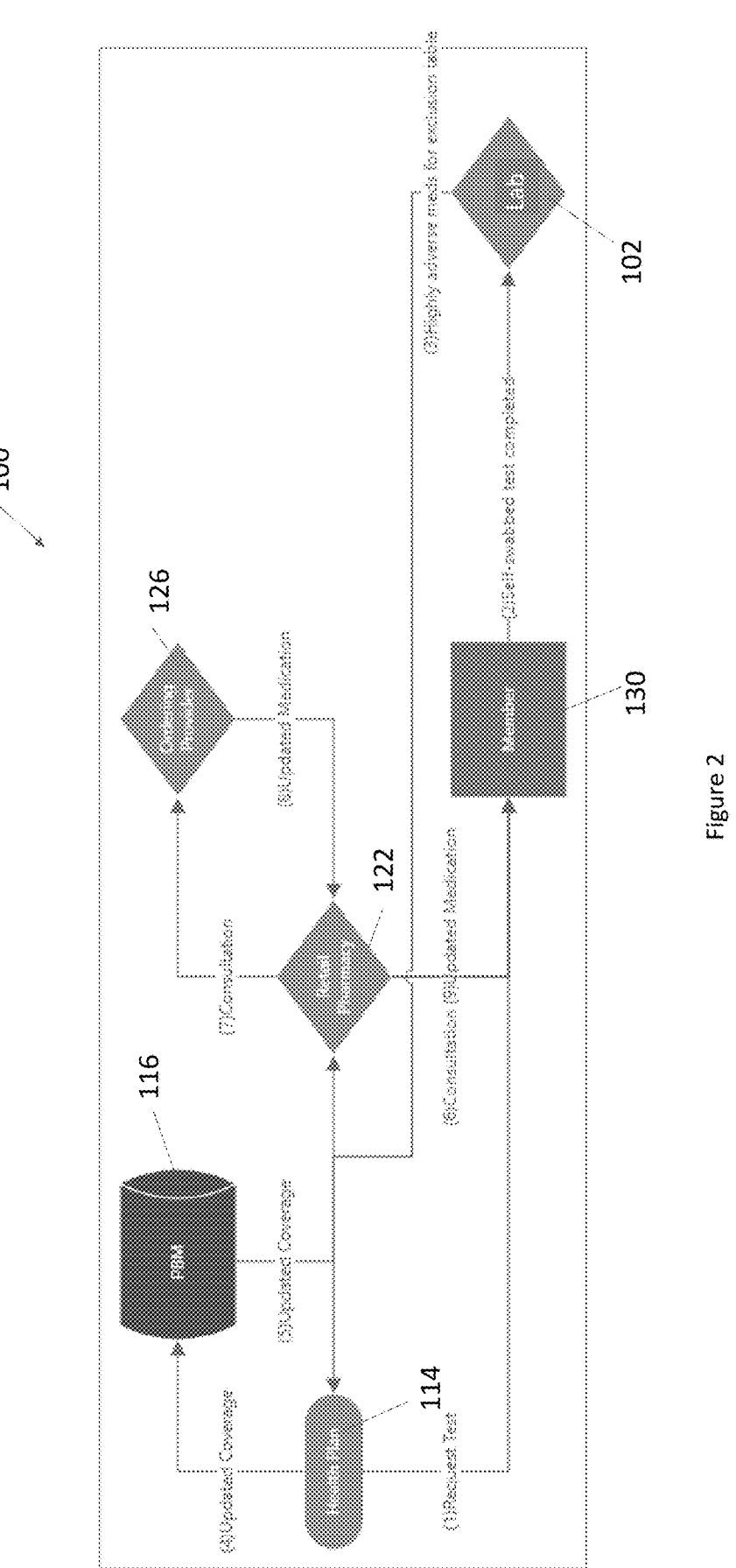
FIG. 2 is a plan view of an exemplary formulary data overlay system and method.

FIG. 2 is an exemplary system and process for generating and utilizing overlays 100 (hereinafter also the "overlay system" or "system"). A health plan 114 may request a test from a member 130 (see item (1)). Such requests may be provided electronically and/or in an automated fashion, though such is not required. The member 130 may consent to testing, such as on an electronic basis, and/or provide a specimen of the member's 130 genetic material to a laboratory 102 which may constitute consent for testing (see item (2)). In exemplary embodiments, without limitation, electronic or other consent from the member 130 may be provided to the laboratory 102 which may generate a testing kit, such as on an automated basis, which is mailed to the member 130 for collecting the specimen.

The laboratory 102 may perform ordered PGx testing on the specimen, such as on an automated basis. The PGx testing may determine the presence or non-presence of the genetic markers for which the testing is performed. The testing to be performed may be specified by the health plan 114, and may be specific to certain medications taken by, or likely to be prescribed to, the member 130. In other exemplary embodiments, the testing may be standard for all members 130.

Based on the genetic test results, medications or other treatments known to be wholly or partially ineffective for the member 130 may be identified and reported to the health plan 114, such as on an automated, electronic basis. Such medications or other treatments may be identified by comparing the member's 130 genetic markers to one or more databases of markers associated with medications or other treatments known to be wholly or partially ineffective in other individuals having the same or similar markers. The testing results may be provided to the health plan 114 for use in an exclusion table in exemplary embodiments (see item (3)). The testing results may be provided to the health plan 114 in the form of one or more overlays. In exemplary embodiments, the overlay(s) may comprise electronic data configured to modify existing formulary data when applied to the formulary. For example, without limitation, the overlay(s) may be configured to cause modifiers to be applied to existing formulary entries, such as on a member-specific basis to reflect the testing results.

The health plan 114 may provide updated coverage modifiers to an associated PBM 116 (see item (4)), such as on an automated electronic basis. Such coverage modifiers may be configured to flag medications known to be partially or wholly ineffective in persons having the same or similar genetic makeup as the member 130. The coverage modifiers may be provided by way of the overlay(s) or otherwise.

The coverage modifiers and/or overlay(s) may be configured to update the PBM 116 to provide one or more codes indicating denial of coverage based on PGx testing results to a retail pharmacy 122 upon querying of a formulary of the PBM 116 for the flagged medication(s) (see item (5)). In exemplary embodiments, without limitation, the coverage modifiers may be provided to the PBM 116 in the form of one or more overlays which are applied to electronically stored formulary data to modify it in a member-specific manner based on the PGx testing results.

Where a retail pharmacy 112 queries the PBM 116 formulary for a medication modified by the coverage modifiers, the code(s) may be returned to the pharmacy 112. The code(s) may indicate denial of coverage. The coverage denials may be initial, such as when testing is available but has not yet been performed. For example, without limitation, coverage approval may be subject to PGx testing and/or a temporarily or limited approval may be provided until testing is performed. Alternatively, the coverage denials may be final, such as where testing has been performed and an indication is made that the medication is wholly or partially ineffective.

Upon receipt of such code(s), the retail pharmacy 112 may consult, such as on an electronic basis, the formulary of the PBM 116 for available alternatives which are not associated with such coverage modifiers (see item (6)). Optionally, the member 130 may also be consulted. The alternatives, if available, may be provided via consultation with an ordering provider 126 (see item (7)). Optionally, the member 130 may also be consulted. In exemplary embodiments, such consultations are provided on an electronic basis by way of one or more electronic health record ("EHR") systems and/or change/modification platforms. The ordering provider 126 may approve or deny the alternative(s). If approved, the updated prescription may be provided to the retail pharmacy 126, such as on an electronic basis via the EHR and/or an e-script system (see item (8)). The member may be informed of the alternative medication, which may be dispensed to the member 130 (see items (6), (9)).

Some or all of the laboratory 102, health plan 114, PBM 116, retail pharmacy 122, ordering provider 126, and/or member 130 may be associated with one or more electronic systems of a same or different type. Such electronic systems may comprise one or more of smartphone, tablets, smart watches, personal computers, servers, electronic storage devices, databases, processors, combinations thereof, or the like.

Figure 3:
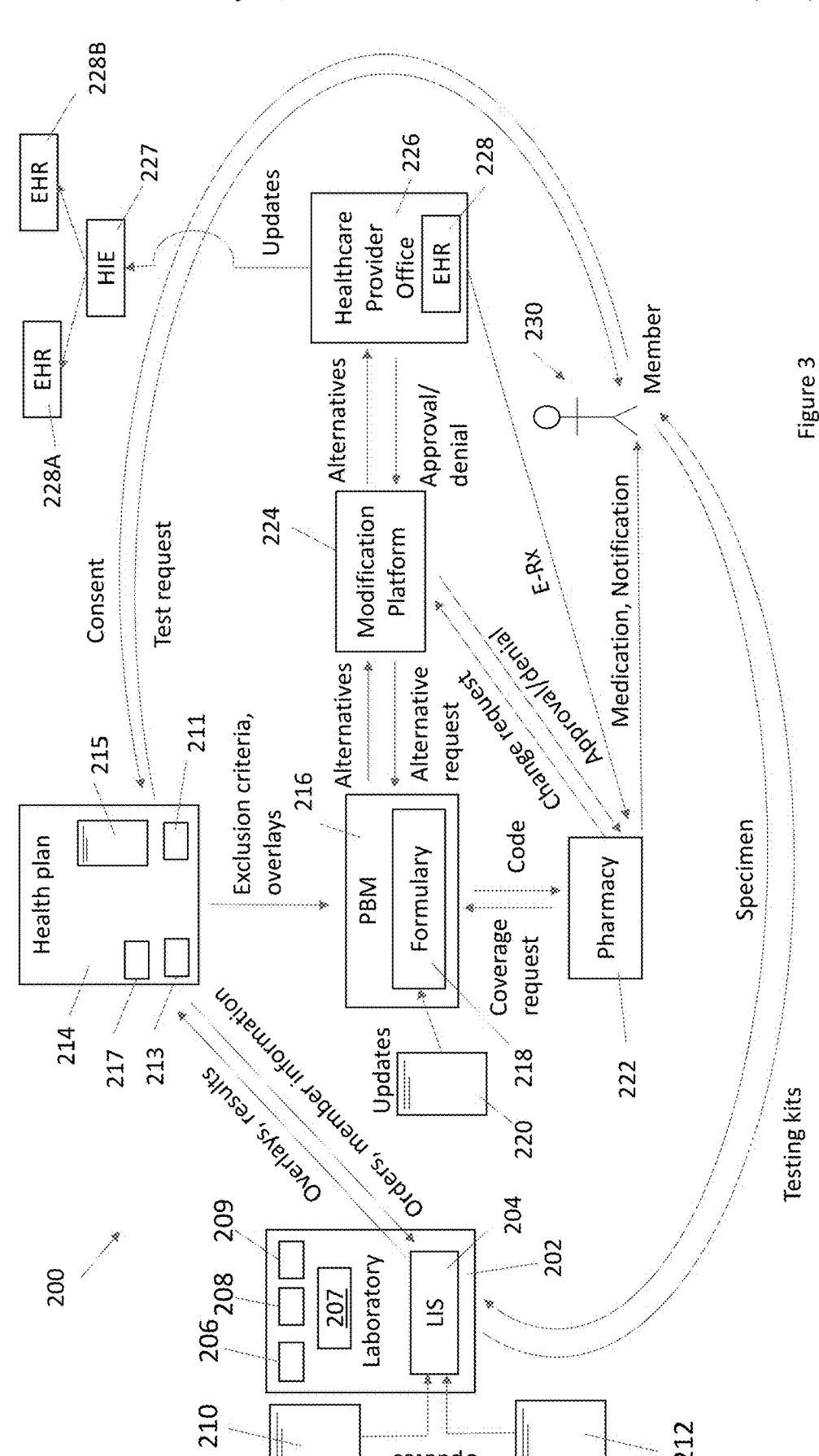
FIG. 3 is a plan view of another exemplary formulary data overlay system.
Figure 6:
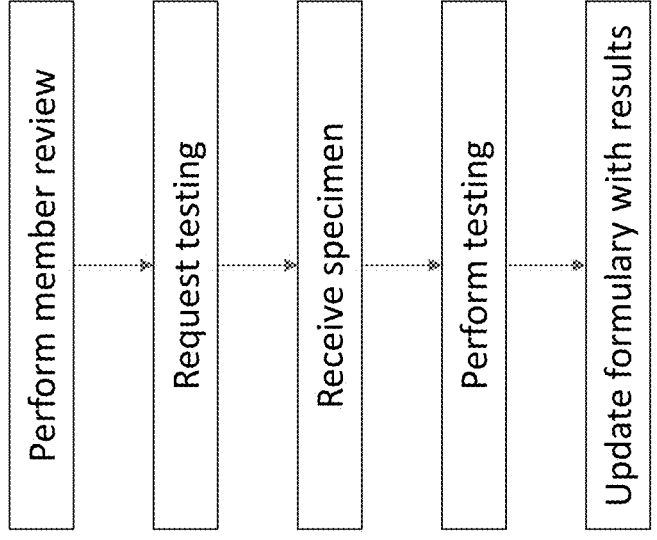
FIG. 6 is a flowchart with exemplary logic for operating the system of FIG. 3.
Figure 7:
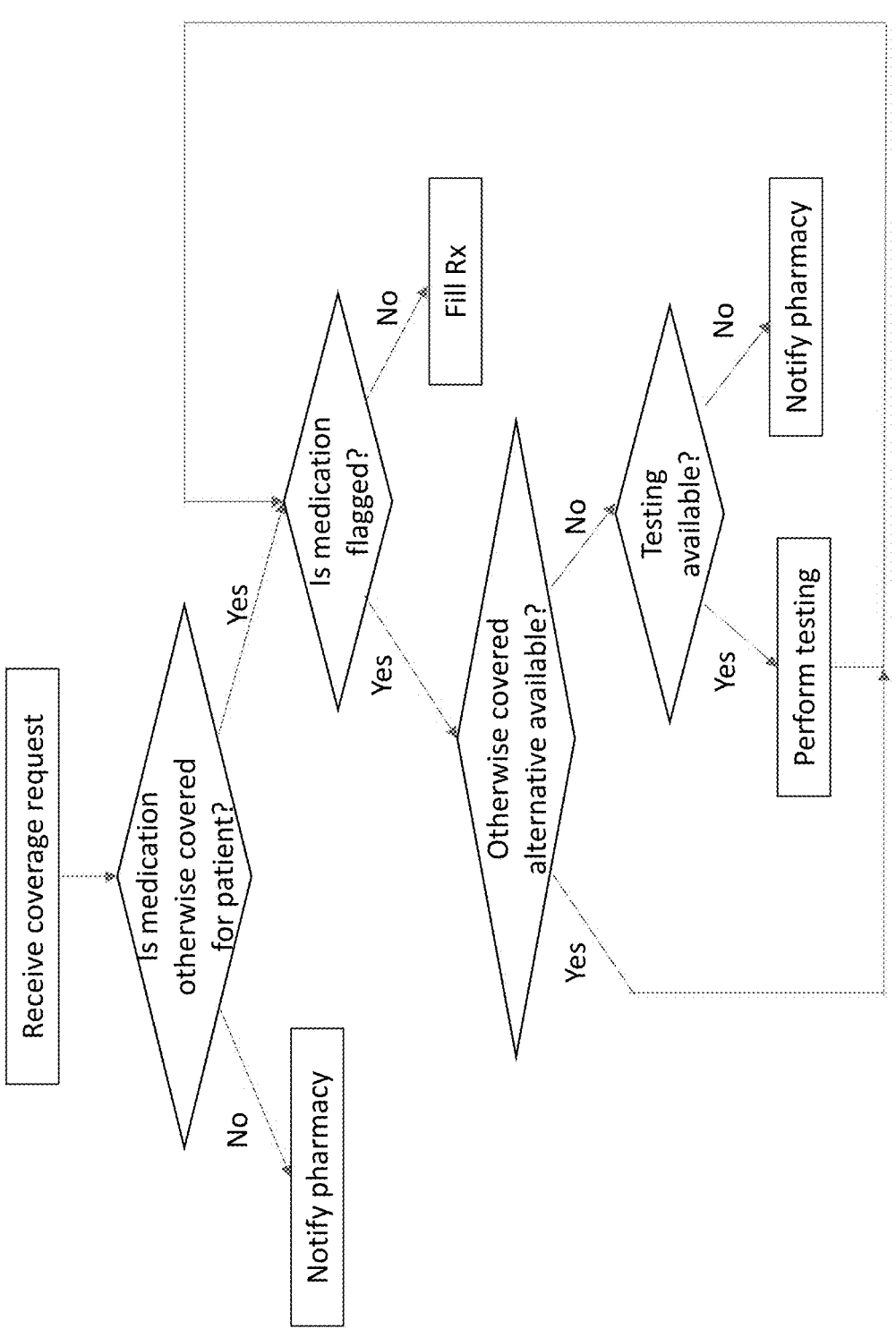
FIG. 7 is flowchart with other exemplary logic for operating the system of FIG. 3.

FIG. 3 is a plan view of another exemplary embodiment of the overlay system 200. Similar items may be numbered similarly but increased by 100 (e.g., 100 to 200, 102 to 202, etc.). FIG. 6 and FIG. 7 illustrate exemplary methods for operating the system 200. The steps shown and/or described may be performed in a different order, repeated, omitted, combinations thereof, or the like.

The system 200 may comprise a health plan system 214. The health plan system 214 may comprise, or be associated with, a member database 215. The member database 215 may comprise member data regarding members 230 of one or more insurance populations, such as, but not limited to, one or more employer health plans. The member data may comprise identifying information and/or medical information for some or all of the members. The member data may include any type or kind of information including, but not limited to, claims data, demographic information, identifying information, contact information, medication lists, treatment history, medical history, diagnosis information, policy information, billing information, cost information, intake information, symptoms, test results, combinations thereof, or the like. The member data may comprise, or be provided in the form of, one or more standardized codes, such as, by not limited to, IDC 10 codes or the like.

The health plan system 214 may comprise, or be associated with, a review module 211. The review module 211 may comprise software instructions, which when executed, configure one or more processors to review member data regarding some or all members 230 of the member database 215. The review module 211 may be configured to trigger or otherwise undertake such a review on an on-demand basis, periodically, occasionally, upon addition/deletion of members 230, following update to the member data for some or all members 230, combinations thereof, or the like. The review module 211 analysis may be limited to that of new members 230 added, of new information added, of an entire population, combinations thereof, or the like.

The review module 211 may be configured to identify a subset of the members 230 which meet various criteria specified by the health plan. Such criteria may include, for example, without limitation, cost information, age, geographic information, weight, lifestyle choices, prescribed treatments, medical history information, current diagnoses information, combinations thereof, or the like. The review module 211 may comprise one or more algorithms and/or filters for applying the criteria to identify the members 230 for testing.

The health plan system 214 may comprise, or be associated with, a notification module 213. The notification module 213 may be configured to, such as on an automated electronic basis, contact the identified members 230 to request PGx efficacy testing. The notification module 213 may comprise one or more of an automated text message system, automated dialer system, automated email system, combinations thereof, or the like. Consent from the member 230, such as, but not necessarily limited to, some or all in the subset of members 230 identified by the review module 211, for testing may be received at the health plan system 214. The notification module 213 may be configured to generate messages informing the member 230 that the testing is zero-cost, that the testing is voluntary, and/or that continued or new coverage approval of certain medications or other treatments is contingent upon completed testing, for example, without limitation.

The health plan system 214 may be configured to electronically transmit information regarding identified members 230, such as, but not necessarily limited to, some or all in the subset of members 230 identified by the review module 211, to a laboratory information system ("LIS") 204 of a laboratory 202 associated with the health plan. The information may include, for example, without limitation, name, mailing address, contact information, combinations thereof, or the like.

Figure 4:
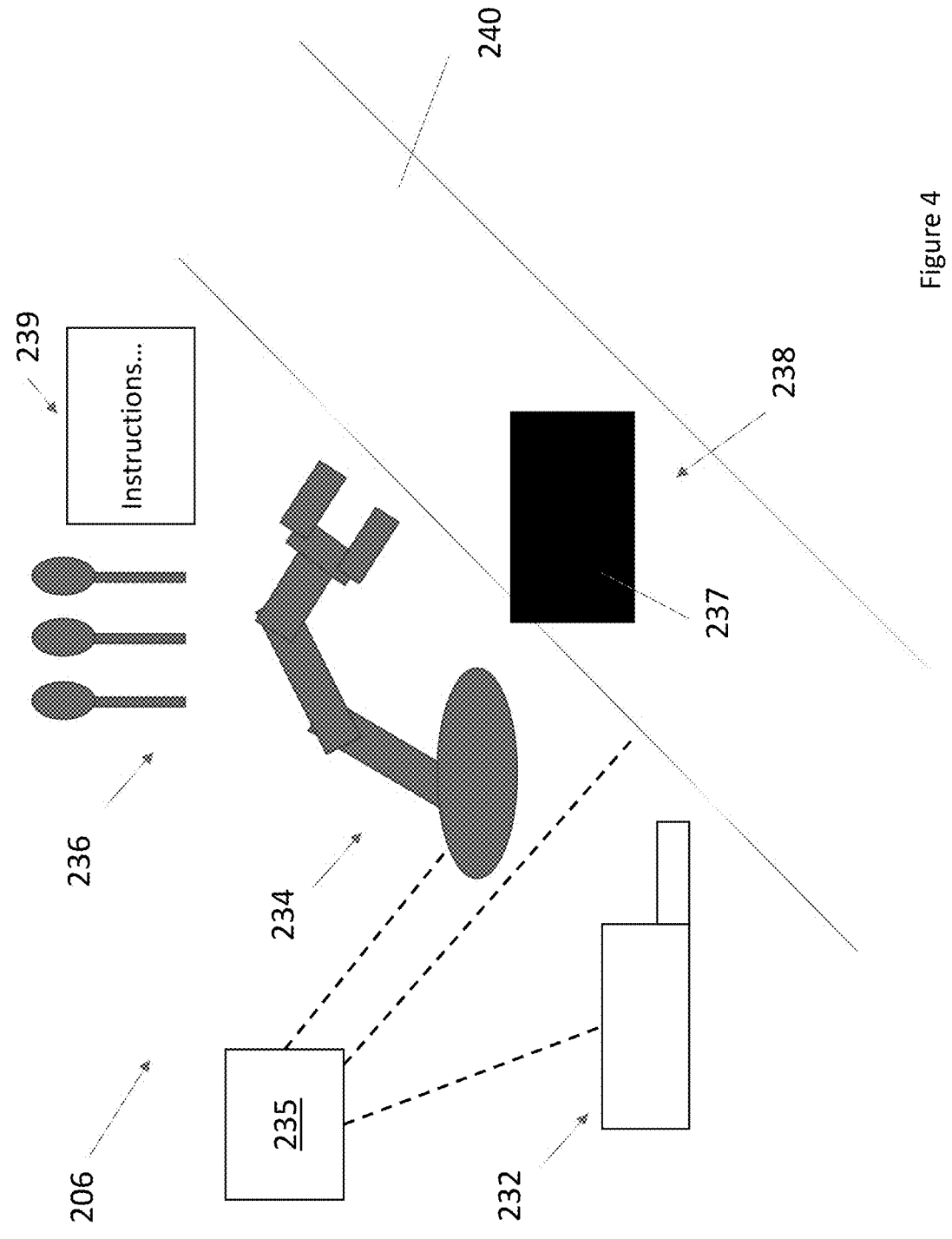
FIG. 4 is a perspective view of an exemplary automated testing kit assembly subsystem for use with the system of FIG. 3.

The LIS 204 may be configured to receive the information for the identified members 230. The laboratory 202 may mail testing kits 238 to each identified member 230. Referring additionally to FIG. 4, in exemplary embodiments, without limitation, the laboratory 202 may comprise a test kit assembly subsystem 206. The test kit assembly subsystem 206 may be partially or fully automated. The test kit assembly subsystem 206 may comprise one or more controllers 235. The controller(s) 235 may be configured to operate one or more material handling robots 234. The material handling robots 324 may be configured to, for example, without limitation, assemble a container 237, insert forms 239 (e.g., consent, invoice, instructions for use, return instructions, combinations thereof, or the like) into the container 237, insert one or more genetic material gathering devices 236 into the container 237, apply labels, operate a printer 232, such as to provide a mailing label for the container 237 to the member 230 and/or a return label for the member 230 to mail the kit 238 back to the laboratory 202, operate a conveyor assembly 240 for the testing kit 238, combinations thereof, or the like. In this fashion, the LIS 204 may be configured to control fully or partially automate assembly of testing kits 238 to the member(s) 230 identified by the health plan system 214. In other exemplary embodiments, testing kits 238 may be, wholly or partially, assembled on a manual basis.

Testing kits 238 may be provided to the members 230, such as by way of common carrier. The member 230 may provide a specimen comprising a sample of the member's

230 genetic material. Provision of the specimen may be a sufficient indication of consent to testing in exemplary embodiments.

The genetic material gathering devices 236 may comprise, for example without limitation, swabs, syringes, vials, strips, combinations thereof, or the like. For example, without limitation, the genetic material gathering device 236 may comprise a swab configured to be used on the inside of the user's cheek to gather saliva and/or skin cells. In other examples, without limitation, the genetic material gathering device 236 may comprise a syringe configured to gather blood, a vial configured to store blood, hair, skin samples, or the like, some combination thereof, or the like. Any type or kind of genetic material gathering device 236 for gathering any type of genetic material may be utilized. The same or varying types of genetic material gathering devices 236 may be utilized. The specimen may be returned to the laboratory 202 for testing, such as by way of common carrier. Components and/or instructions for the return of the specimen may be included in the testing kit 238.

Figure 5:
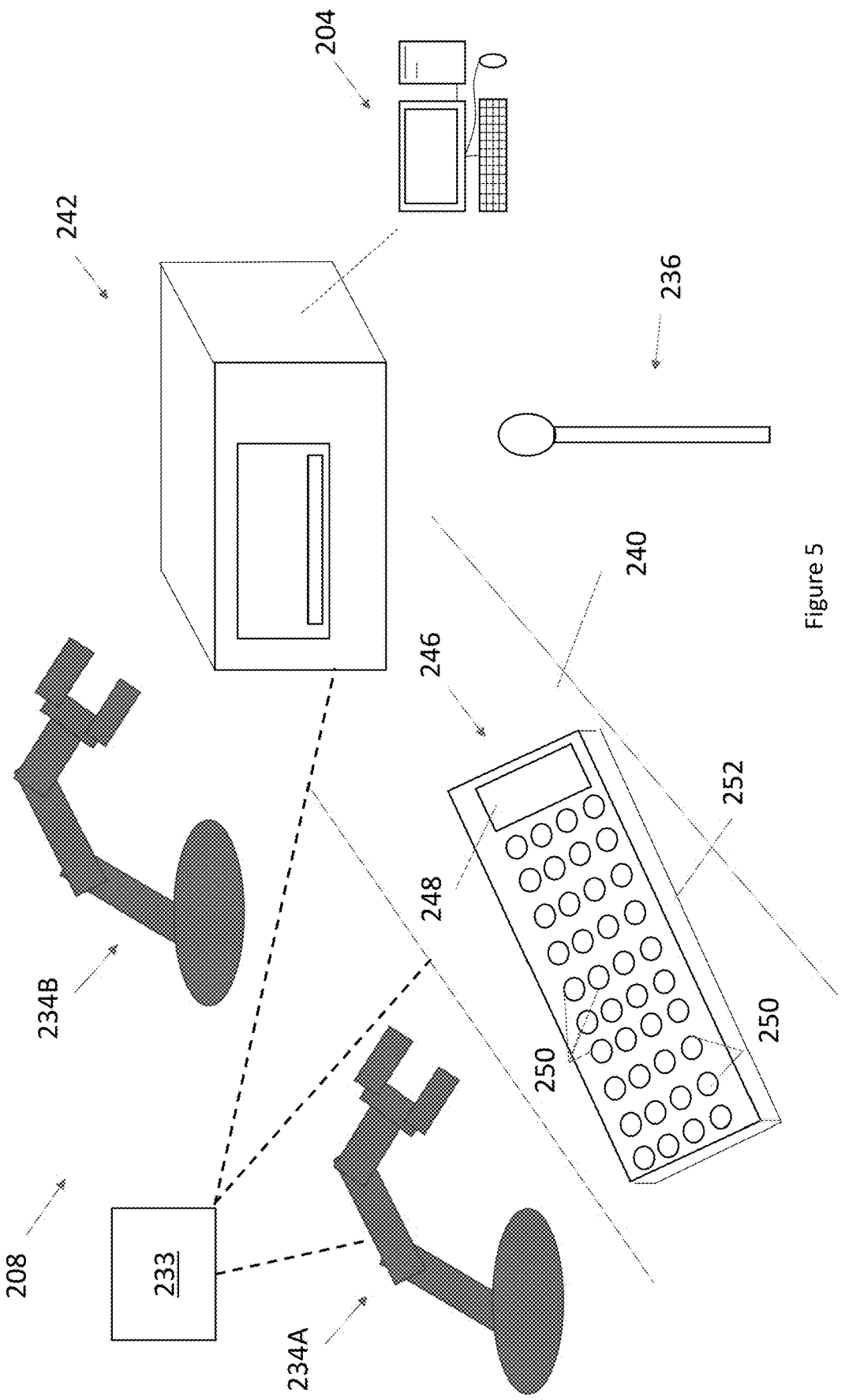
FIG. 5 is a perspective view of an exemplary automated testing performance subsystem for use with the system of FIG. 3.

The laboratory 202 may perform ordered genetic testing on the received specimens. Referring additionally to FIG. 5, in exemplary embodiments, without limitation, the laboratory 202 may comprise an automated testing subsystem 208. The automated testing subsystem 208 may comprise one or more controllers 233.

The controller(s) 233 may be configured to operate one or more material handling robots 234. The material handling robots 234 of the testing subsystem 208 may be the same or different from the material handling robots 234 of the test kit assembly subsystem 206. In exemplary embodiments, without limitation, a first subset of the handling robots 234B may be configured to assemble a genetic testing device 246. The genetic testing device 246 may comprise a chip 252 comprising a number of wells 250 in exemplary embodiments, though any type or kind of testing devices 246 of the same or different type may be utilized. Each of said wells 250 may be configured to test for a particular genetic marker. The testing device 246 may be configured to accommodate any number of wells 250. In exemplary embodiments, certain wells 250 may be added or removed from the testing device 246 in order to test for the presence or non-presence of various genetic markers. For example, without limitation, wells 250 may be added to the chip 252 to test for particular genetic traits and wells 250 may be removed from the chip 252 if a particular genetic trait is not being tested for. In still other exemplary embodiments, the wells 250 being used may be placed in an unblocked position such that genetic material may enter the well 250. Similarly, the wells 360 not being used may be placed in a blocked position such that genetic material may not enter the wells 250. The testing device 252 may comprise one or more areas 248 to affix labels, markers, or the like, and may comprise, for example, without limitation, unique identifiers, barcodes, QR codes, some combination thereof, or the like. Modifications to the testing device 252 may be performed automatically by the first set of handling robots 234 in accordance with instructions from the controller 233 based on the ordered testing.

The first and/or a second subset of material handling robots 234B may be configured to apply the specimen, such as by way of the genetic material gathering devices 236 to the testing devices 252 for testing.

The controller(s) 233 may be configured to operate a second subset of material handling robots 234B. The second subset of material handling robots 234B may be configured to move the testing devices 246 into one or more genetic sequencing machines 242 and/or operate the genetic sequencing machines 242. Alternatively, or additionally, the controller(s) 233 may be configured to operate the genetic sequencing machines 242.

The genetic sequencing machines 242 may be of any type or kind. In exemplary embodiments, the genetic sequencing machines 242 may comprise a loading area and/or a control panel. The loading area may be configured to accept one or more testing devices 246. The control panel may be integrally formed with the genetic sequencing machines 242 or may be a separate electronic device in communication with the genetic sequencing machines 242. The control panel may be configured to accept manual user input comprising instructions for carrying out various genetic tests on the testing machines 242. The control panel may be configured to display the results of such testing. Such instructions may, alternatively, or additionally, be accepted from a remote device, such as the LIS 204 and/or controller(s) 233, which may operate as the control system for the genetic sequencing machines 242. Testing results may be transmitted to one or more remote devices, such as the LIS 204 and/or controller (s) 233, and/or systems as further described herein.

The controller(s) 233 may be configured to operate one or more conveyor systems 240 for moving the testing kit 246, genetic material gathering devices 236, combinations thereof, or the like.

Alternatively, or additionally, some or all of the testing may be performed wholly or partially on a manual basis, such as with the aid of one or more genetic sequencing machines 242.

The LIS 204 may serve as the controller(s) 235 and/or controller(s) 233, in exemplary embodiments without limitation.

Test results may be electronically reported to the LIS 204, such as from the genetic sequencing machines 242.

The LIS 204 may comprise, or be associated with, a database of treatments, such as, but not necessarily limited to, medications, known to be wholly and/or partially effective in persons having particular genetic makeup(s) 210 (hereinafter also the "PGx treatment efficacy database"). Such information may be gathered from one or more public or private sources such as, but not limited to, the human genome project. The PGx treatment efficacy database 210 may be updated periodically, such as when new information is obtained regarding medications or other treatments known to be wholly or partially ineffective in persons having particular genetic makeups. Such updates may be provided to the LIS 204 in exemplary embodiments, without limitation.

The LIS 204 may be configured to automatically compare the member's 230 reported genetic makeup against the PGx treatment efficacy database 210 to determine if certain treatments are wholly or partially ineffective for the member 230. The LIS 204 may be configured to report such results to the health plan system 214. Such results may be provided in the form of an electronic report. In exemplary embodiments, the results may be provided by way of one or more updated exclusion tables and/or updates to existing exclusion tables. Additional copies of the results may be reported to other parties, including, but not limited to, the member 230, such as on a courtesy basis.

The results may list all known treatments known to be wholly or partially ineffective for the member 230. Alternatively, or additionally, the results may be compared against actually prescribed and/or likely to be prescribed medications for the member 230, such as, but not limited to, those commonly prescribed to treat conditions associated with the member 230. In exemplary embodiments, the report may comprise color coded results. For example, without limitation, red color coding may indicate an ineffective treatment and/or dosage. A yellow color coding may indicate the need to adjust the treatment and/or dosage or monitor use of the therapy. A green color coding may indicate that the treatment and/or dosage is acceptable. Other colors and types of coding may be utilized.

The health plan provider system 214 may be configured to automatically generate exclusion criteria in accordance with the testing results. The health plan system 214 may comprise, or be associated with, a modifier module 217. The modifier module 217 may comprise software instructions, which when executed, configure one or more processors to generate exclusion criteria for a formulary 218. In exemplary embodiments, without limitation, the formulary 218 may be stored at, or otherwise associated with, a PBM system 216. The exclusion criteria provided by the modifier module 217 may be configured to cause the formulary 218 to update with member and/or plan specific criteria, such as on a medication specific basis, member 230 specific basis, plan specific basis, combinations thereof, or the like. For example, without limitation, the exclusion criteria may be configured to prevent, flag, or limit approval of medications or other treatments known to be wholly or partially ineffective in persons having the same genetic makeup as the member 230 in accordance with the reported results. The exclusion criteria may be applied to one or more formularies 218. The exclusion criteria, in exemplary embodiments, may be provided in the form of one or more overlay(s) or the same or different type.

Alternatively, or additionally, the LIS 204 may comprise, or be associated with, an overlay generation module 209. The overlay generation module 209 may be configured to generate overlays based on the PGx testing results, such as on a member 230 specific basis. The overlays may be transmitted to the health plan system 214 and/or the PBM system 216 to update the formulary 218, such as on an automated, electronic basis. The formulary 218 may be updated following receipt of such overlays such as on an automated, electronic basis. The overlays may comprise electronic data configured to modify the formulary 218 in accordance with the PGx results. The overlays may be configured to electronically interface with the formulary 218 directly or indirectly. For example, without limitation, the one or more overlays may be configured to electronically generate the exclusion criteria, create member-specific information with the formulary 218, and/or create member-specific versions of the formulary 218. The overlays may be configured to directly modify the formulary 218, for example, without limitation.

The overlay(s) may be configured to cause each and every treatment known to be wholly or partially ineffective in persons having the same genetic makeup as the member 230, such as reported in the PGx testing results as compared to the PGx treatment efficacy database 210 by the LIS 204, to be flagged in the formulary 218 such that one or more codes are generated upon request for coverage for such treatments. The codes, in exemplary embodiments, may comprise one or more PGx-specific codes. The codes may be standardized codes, including, but not limited to, those provided by the NCPDP, though such is not required. The codes may be configured to indicate, for example, without limitation, "Dispensing Not Authorized Due to Laboratory Test Results" or the like at that PBM system 216 and/or a pharmacy system 222 following receipt. In this manner, billing information stored at the formulary 218 may be automatically and electronically returned with any PGx-specific codes, for example, without limitation. The billing information may include, but is not necessarily limited to, costs, discounts, covered costs, out of pocket expenses, combinations thereof, or the like. The billing information may be provided as one or more standardized billing codes, though such is not required While PGx-specific information is discussed in some places herein, other clinical information may be provided at the overlays for integration with the formularies 218. In this manner, the system 200 may operate to provide member related safety alerts. The alerts may be based on PGx data or other clinical data, and may be related to, for example, without limitation, potential safety issues surrounding allergies, efficacy, interactions, recalls, dosing, combinations thereof, and the like. Any type of kind of data may be provided with the overlays and may relate to any member issues, safety or otherwise.

While illustrated as being associated with the PBM system 216, the formulary 218 may be associated with the health plan provider system 214, the LIS 204, the pharmacy system 222, or otherwise. The overlays may be provided directly or indirectly from the LIS 204 and/or the health plan system 214 to the formulary 218, which may be associated with the PBM system 216, the health plan system 214, or separate therefrom.

The health plan system 214, PBM system 216, and/or LIS 204 in exemplary embodiments, may be configured to automatically and electronically perform an available alternatives analysis for all treatments flagged as being partially or wholly ineffective for the member 230, though such is not required. Such alternatives may be identified by way of the formulary 218.

The LIS 204 may comprise, or be associated with, an available PGx testing database 212. The available PGx testing database 212 may comprise data regarding PGx testing available for certain treatments. The available PGx testing database 212 may, alternatively, or additionally, comprise data regarding PGx testing available under certain insurance policy criteria, policy rules, such as under certain health plans, medically necessary criteria, combinations thereof, or the like. The available PGx testing database 212 may be updated periodically, such as when new information is obtained regarding medications or other treatments known to be wholly or partially ineffective in persons having particular genetic makeups, testing agreements are established or changed, new tests are developed, combinations thereof, or the like. Such updates may be provided to the LIS 204 in exemplary embodiments, without limitation.

In exemplary embodiments, the LIS 204 may be configured to provide information regarding available PGx testing from the available PGx testing database 212 to the health plan system 214. In exemplary embodiments, such information is provided as one or more overlay(s), such as by way of the overlay generation module 209, though such is not required. The health plan system 214, such as but not limited to the review module 211 may utilize this information as one or more of its criteria for identifying members 230 for testing.

The system 200 may be configured to, alternatively, or additionally, prompt PGx efficacy testing where new prescriptions are generated, transmitted, and/or received. Prescriptions, such as electronic prescriptions (hereinafter also "e-Rx") may be provided from a health care provider system 226, such as by way of one or more electronic health record ("EHR") systems, to the pharmacy system 222 for a particular one of the members 230. The pharmacy system 222 may be configured to query the formulary 218 of the PBM system 216 associated with the member 230, such as for coverage information. The formulary 218 may be as modified by one or more overlays, such as indicating available PGx efficacy testing and/or PGx testing results.

The health care provider system 226 and/or EHR system may be associated with any type of healthcare provider including, but not limited to, primary care providers, specialists, hospitals, clinics, urgent care facilities, hospice providers, nursing homes, rehab facilities, testing centers, health centers, government facilities, private facilities, combinations thereof, or the like.

Where a coverage request is received from the pharmacy system 222 for a treatment flagged in the formulary 218 as wholly or partially ineffective for the member, the PBM system 216 may be configured to automatically and electronically generate and transmit PGx-specific code(s) to the pharmacy system 222. The codes may indicate that testing is available for the treatment and/or that testing results indicate a prescribed treatment to be partially or wholly ineffective for the member 230. Upon receipt of such PGx-specific code(s), the pharmacy system 222 may be configured to generate a change request.

The change request may be transmitted to a modification platform 224 and/or the PBM system 216. The formulary 218 may comprise, or be electronically associated with, one or more alternative treatment option databases 220. The alternative treatment option database 220 may comprise one or more alternative treatments, each associated with one or more other treatments, where the alternative treatments are those known to be wholly or partially effective alternatives to the treatments flagged in the formulary 218 as being wholly or partially ineffective for the member 320. The alternative treatment option database 220 may be queried to return one or more alternative treatment options associated with the treatments identified by the formulary 218 as being wholly or partially ineffective for the member 230 in accordance with the PGx results and/or indicate a lack of available alternatives.

The alternative(s), if available, may be presented to the healthcare provider for approval. In exemplary embodiments, such alternatives are presented electronically by way of the modification platform 224 at the EHR system 228. The healthcare provider may approve or deny such alternative(s). If denied, an option to cancel the order may be provided at the modification platform 224. If one or more alternatives are approved, the approval for the alternative(s) may be returned, such as by way of the modification platform 224, to the pharmacy system 222 and/or the PBM system 216.

The EHR system 228 may be automatically and electronically updated, such as by the modification platform 224, to reflect the prescription of the approved alternative(s) in lieu of the originally prescribed treatment(s). This may reduce or prevent a number of otherwise needed communications, typically by phone, between the healthcare provider and/or representatives of the healthcare provider's office and the pharmacy staff.

The formulary 218 may be configured to return billing information with any approved treatment options, including, but not limited to, the alternative(s) to the pharmacy system 222. In this manner, the member 230 may be provided with exact cost information (e.g., total cost, covered costs, out-of-pocket expenses, combinations thereof, or the like) in advance, such as prior to arrival or shipping of the medication. Such information may be transmitted electronically by the pharmacy system 222 to one or more electronic devices associated with the member 230, in exemplary embodiments, without limitation, such as prior to the approved treatment(s) being filled.

The member 230 may be notified of any approved alternative(s), which may then be filled as needed.

The treatment information, including, but not limited to, any alternative(s) approved, may additionally be provided to a number of other authorized parties 228A, 228B associated with the member 230, such as direct from the LIS 204 and/or by way of one or more intermediaries, such as, but not limited to, health care information exchange ("HIE") systems 227, though such is not required. Such authorized parties may include, but are not limited to, pharmacists, project managers, healthcare practice administrators, insurance providers, users, other healthcare providers, other approved persons, and the like.

In exemplary embodiments, without limitation, the results of the PGx testing may be integrated with the EHR system 228 by way of the LIS 204, the modification platform 224, and/or the PBM system 216, though such is not required. In exemplary embodiments, without limitation, the PGx efficacy testing results may be automatically and electronically designated as an allergy in the member's 230 file at the EHR system 228. Existing EHR systems 228 may not have a dedicated space for the integration of genomic testing results. Redesigning existing EHR systems 228 to provide such a dedicated space would be time consuming and expensive. Many, if not all, existing EHR systems 228 have a designated space for the notation of allergies. As such, this provides an available pathway for integration of genomic efficacy testing results into the member's electronic file. Existing EHR systems 228 may be configured to automatically generate an alert or otherwise provide a notification, upon prescription of such treatments flagged as an allergy. In this way, for example, without limitation, ineffective medications and/or dosages may be subsequently alerted to the healthcare provider when ordering at the EHR system 228.

In exemplary embodiments, the formulary 218 may be configured to automatically generate one or more codes, such as, but not limited to, standardized codes, reporting that PGx efficacy testing is available for a queried treatment. The formulary 218 may be so configured by way of one or more overlay(s), such as in accordance with the available PGx testing database 212 information as generated by the overlay generation module(s) 209.

The overlays may be configured to cause the PBM system 216 to automatically trigger one or more of a proposed order generation, pre-authorization review, order approval, member consent, insurance coverage review, and/or payment collection for such PGx testing upon query of treatments at the formulary 218 associated with available PGx testing, particularly where no reported PGx testing results are found. Alternatively, or additionally, the overlays may be configured to cause the PBM system 218 to generate one or more codes or other unique identifiers, indications, notifications, flags, combinations thereof, or the like for transmission to the pharmacy system 222, the EHR system 228, the health plan provider system 214, the LIS 204, combinations hereof, or the or like, indicating the availability of PGx efficacy testing for the treatment(s), proposed orders for such testing, pre-authorization review, order approval, member consent, insurance coverage review, and/or payment collection, combinations thereof, or the like. The overlay(s) may be configured to only provide such codes or other unique identifiers, indications, notifications, flags, combinations thereof, or the like where no PGx test results are stored for the member 230 at the associated treatment. Alternatively, or additionally, the overlay(s) may be configured to remove the available PGx testing codes or other unique identifiers, indications, notifications, flags, combinations thereof, or the like where such test results are already stored for the member 230 or are later added. In this manner, medications or other treatments for which PGx testing may be applicable may be automatically determined and commenced. This may be in alternative to, or in addition to, flagging clinical data within the overlays, such as PGx test results. Separate overlays may be provided for each, or the same overlay may be used and/or updated.

In exemplary embodiments, without limitation, the LIS 204 and/or health plan system 214 may be configured to update the overlays denoting available PGx testing, such as periodically, on-demand, occasionally, combinations thereof, or the like. Such updates may be in accordance with updates to the databases 210 and/or 212, for example. The updates may be configured to indicate availability of new or additional PGx testing, approval of PGx testing for coverage, and/or other medications or treatments newly or otherwise known to be wholly or partially ineffective or wholly or partially effective in person's having particular genetic makeups. In this manner, the overlays may be kept current. Such updated overlays may be automatically updated with updates to the various databases, such as databases 210, 212, 220, combinations thereof, or the like. Such updates may be made by way of modified overlays, new overlays, combinations thereof, or the like. Such updates may be pushed using translational software in exemplary embodiments. Being a cutting-edge field, PGx efficacy testing is sometimes unknown or under-considered by health plan providers. The disclosed systems and methods help ensure that the member 230 receives the highest quality of care and maximizes the information available to health plan providers.

In exemplary embodiments, the formulary 218 may be configured to return approval for a partial, limited, one-time only, combinations thereof, or the like approval of a medication to the pharmacy system 222 upon query of a treatment where available PGx testing is noted as available but not yet performed. Further fill of the medication may be indicated as contingent on member 230 completion of the available PGx testing.

Some or all of the components of the system 200 may be remote from one another. For example, without limitation, sequencing machines 242, the LIS 204, and other components of, or associated with, the laboratory 202 may be located in the same physical facility, or may be remote from one another. The electronic communication may be by way of wired and/or wireless connections. The electronic communication may further be made by way of one or more network interface devices and one or more communication networks located at each of the various components of the system 200. The communication networks utilized may include, but are not limited to, the internet, intranet, cellular network, or the like. In exemplary embodiments, some or all of communications may be made secured and encrypted. Alternatively, or additionally, such communications may be made in a standardized format such as, but not limited to, an HL7 format and/or by way of a PathX HL6 electronic communication, that are received and embedded into any .pdf type files generated from the HL7 file.

Alternatively, or in addition, various items of information of the system 200, such as, but not limited to, the PGx test results, may be made available by way of one or more internet-based portals. Access to such information may be permission based. For example, without limitation, permission may be set such that login credentials associated with a given individual or group may permit access to test results for particular members 230. Access to the information, including, but not limited to, testing results, may be protected by way of security protocols, such as, but not limited to, authentication, biometric scanning, single sign-on, barcode scanning protocols, some combination thereof, or the like. The automation and reduction in human interaction provided by the disclosed systems and method may reduce the number of potential intrusion points and improve data security.

Each of the various systems shown and/or described herein, including, but not limited to, the LIS 204, the health plan system 214, the PBM system 216, the pharmacy system 222, the EHR system 228, may comprise one or more electronic components. Such electronic components may include, but are not limited to, processors, electronic storage devices, user input devices, displays, and the like. Such electronic components may take the form of computers, servers, smartphones, tablets, some combination thereof, or the like, though such is not necessarily required. Each of the systems may comprise software instructions configured to perform the steps and functions described herein.

As information is transferred between certain components of the system 200, it may be converted from a file format specific to the system, subsystem, and/or components used by the transmitting component and a common format for transfer. Such conversion may happen at the transmitting component, at a common module, a dedicated appliance, the LIS 204, combinations thereof, or the like. The common formatting information may subsequently be transferred and converted into a format specific to the receiving component. Such conversion may happen at the receiving component, at a common module, a dedicated appliance, the LIS 204, combinations thereof, or the like. Regardless, the transferred information may flow through the LIS 204, in exemplary embodiments, which may act as a hub for the control and distribution of such information. The LIS 204 may exclusively comprise information in the common format, though such is not required. The LIS 204 may be configured to build a database of information as such information is passed through the LIS 204, such as to other components of the system 200.

Databases shown and/or described herein, including, but not limited to, the member database 215, the PGx treatment efficacy database 210, the available PGx testing database 212, and/or the alternative treatment option database 220, may comprise multiple servers and/or electronic storage devices. Portions of the data may be stored within various individual databases which collectively makeup the various database(s) on an individual or collective basis. For example, without limitation, the member database 215 may comprise multiple individual databases which collectively makeup the member database 215.

Figures 8, 9A, 9B:
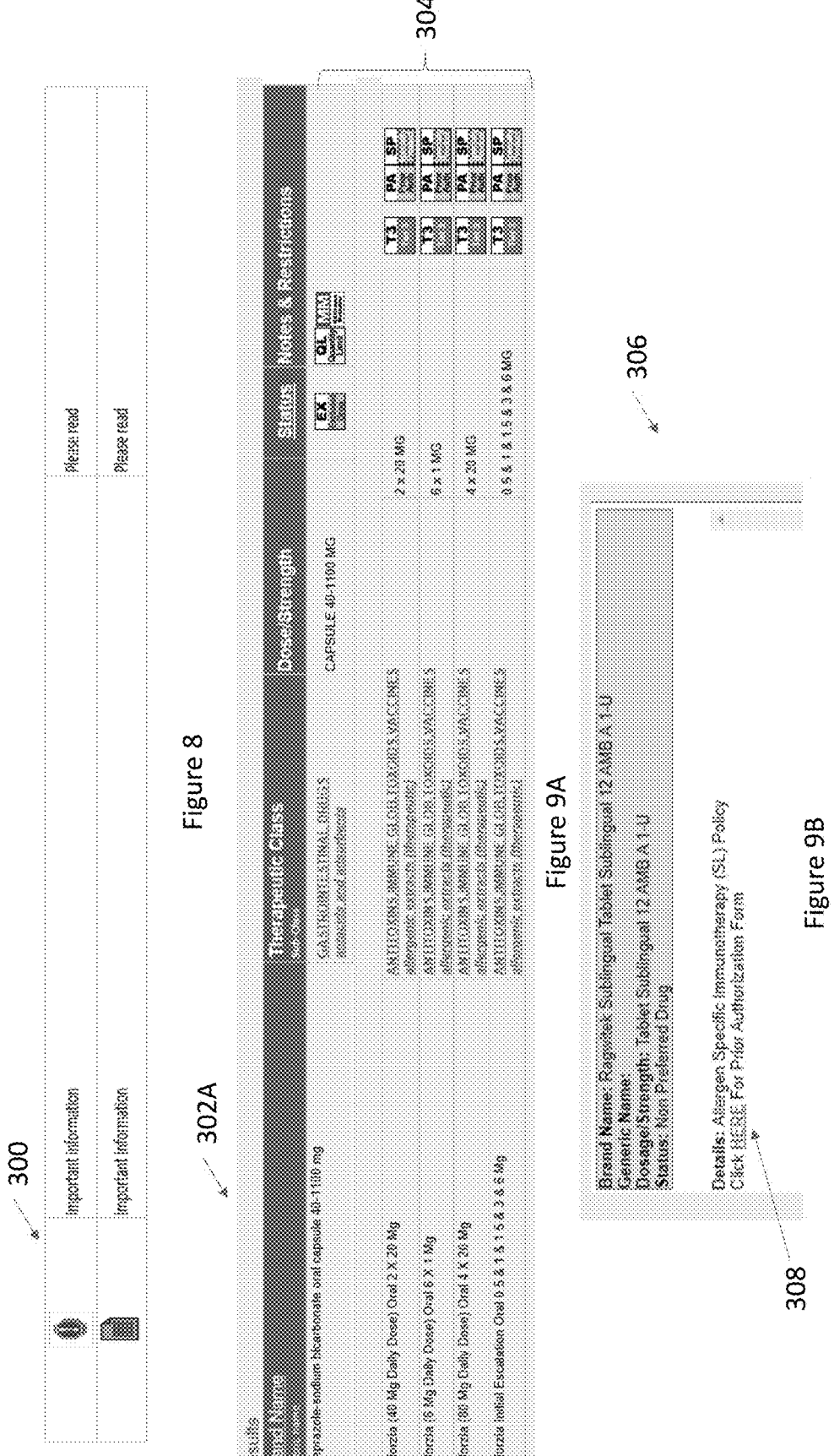
FIG. 8 is an exemplary indicator generated by the system of FIGS. 2-3.
FIG. 9A is an exemplary medication report generated by the system of FIGS. 2-3.
FIG. 9B is an exemplary pre-authorization request prompt for the medication report of FIG. 9A.

FIG. 8 illustrates exemplary PGx indicators 300. The PGx indicators 300 may be generated by the systems 100, 200 in exemplary embodiments. For example, without limitation, one or more of the PGx indicators 300 may be generated upon query of treatments of the formulary 218 modified by one or more overlays in a manner indicating available PGx testing and/or partially and/or wholly ineffective treatments, such as medications, for the member 230. The types and kinds of PGx indicators 300 illustrated are merely exemplary and are not intended to be limiting. Any type or kind of PGx indicators 300 may be utilized. The PGx indicators 300 may be generated or provided at one or more displays, portals, or the like and may comprise links to additional information, such as further information regarding available PGx testing and/or partially and/or wholly ineffective nature of the queried medications for the member 230. The PGx indicators 300 may be generated or provided upon querying of treatments associated with exclusion criteria, modifiers, overlays, combinations thereof, or the like.

Figures 10A, 10B:
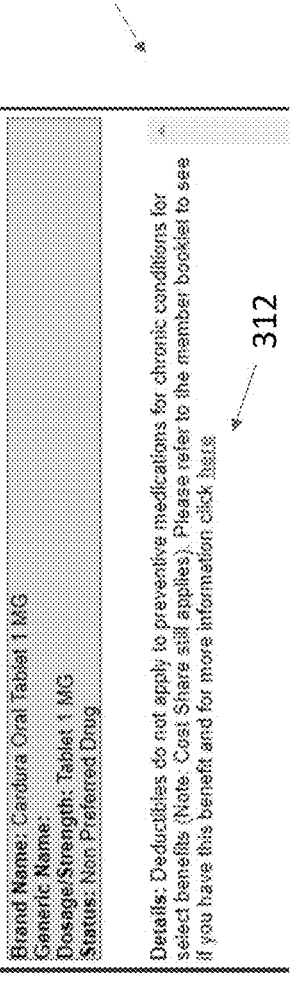
FIG. 10A is another exemplary medication report generated by the system of FIGS. 2-3.
FIG. 10B is an exemplary billing information prompt for the medication report of FIG. 10A.
Figure 11:
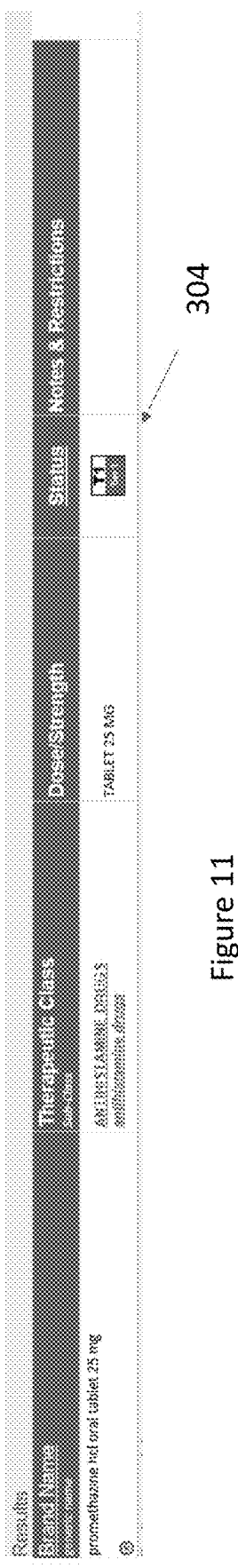
FIG. 11 is another exemplary medication report generated by the system of FIGS. 2-3.

FIG. 9A, FIG. 10A, and FIG. 11 illustrate various exemplary medication reports 302A, 302B, 302C. The medication reports 302 may be generated by the systems 100, 200 upon querying of the formulary 218 for particular treatments, in exemplary embodiments. The medication reports 302 may comprise various identifying and dosing information for the medications. The medication reports 302 may comprise one or more indicators 304, including, but not limited to, the PGx indicators 300. The indicators 304 may comprise icons, flags, graphics, images, text, audio, combinations thereof, or the like. Any number, type, or kind of indicators 304 may be utilized. A legend 308, such as illustrated with regard to FIG. 12 may be generated or otherwise made available upon demand which explains the nature of the indicators 304. The indicators 304 may comprise status indicators and/or notes and restrictions indicators, the latter may include, but is not limited to, the PGX indicators 300. The systems 100, 200 may be configured to generate and incorporate the indicators 304 as appropriate, such as, but not limited to, in accordance with the formulary 218 as modified by one or more overlays, into the various medication reports 302.

As illustrated at FIG. 9B, the systems 100, 200 may be configured to automatically provide a prior authorization prompt 306 for queried medications which are flagged as requiring prior authorization. The prior authorization prompt 306 may comprise a feature for automatically generating a prior authorization request 308. As illustrated at FIG. 10B, the systems 100, 200 may be configured to automatically provide a billing information report 310 for medications, such as those with special billing provisions according to health plan 114, 214 rules for the member 230. The billing information report 310 may comprise a feature for automatically generating additional information and/or collecting payment 312.

Modules shown and/or described herein may comprise executable software instructions, algorithms, filters, combinations thereof, or the like.

Any embodiment of the present invention may include any of the optional or preferred features of the other embodiments of the present invention. The exemplary embodiments herein disclosed are not intended to be exhaustive or to unnecessarily limit the scope of the invention. The exemplary embodiments were chosen and described in order to explain the principles of the present invention so that others skilled in the art may practice the invention. Having shown and described exemplary embodiments of the present invention, those skilled in the art will realize that many variations and modifications may be made to the described invention. Many of those variations and modifications will provide the same result and fall within the spirit of the claimed invention. It is the intention, therefore, to limit the invention only as indicated by the scope of the claims.

Certain operations described herein may be performed by one or more electronic devices. Each electronic device may comprise one or more processors, electronic storage devices, executable software instructions, and the like configured to perform the operations described herein. The electronic devices may be general purpose computers of specialized computing device. The electronic devices may be personal computers, smartphone, tablets, databases, servers, or the like. The electronic connections described herein may be accomplished by wired or wireless means. The computerized hardware, software, components, systems, steps, methods, and/or processes described herein may serve to improve the speed of the computerized hardware, software, systems, steps, methods, and/or processes described herein.

What is claimed is:

1. A method for automatically alerting, at the point of prescribing or prescription fulfilment, using interoperable, standardized messaging, to wholly or partially ineffective medications for a member based on the member's relevant genetic makeup and updating electronic medical records data comprising patient data stored at an electronic health record ("EHR") system for the member, said method comprising the steps of, electronically and automatically:

causing, by way of a laboratory information system ("LIS") associated with a laboratory and exerting operative control over one or more genetic sequencing machines, genetic testing to be carried out;

receiving, from the one or more genetic sequencing machines, genetic testing results data at the LIS;

generating a data interface overlay, by way of the LIS, including the genetic testing results data and configured to create member-specific modifications to existing data of a formulary upon application thereto;

transmitting, by way of the LIS, the data interface overlay to one or more non-transitory electronic storage devices comprising the formulary for integration therewith, thereby creating, following receipt, the member-specific modifications to existing data of the formulary such that a pharmacy benefits manager ("PBM") system is configured to cause automatic generation of a standardized code upon subsequent querying in responses to receiving standardized requests for coverage information for members and medications indicated in the modified data as being known to be partially or wholly ineffective in persons having a same relevant genetic makeup as the members according to the genetic testing results data ("genetic contraindication code");

generating, by way of the LIS, a second data interface overlay including available but unperformed, genetic testing for medications;

transmitting, by way of the LIS, the second da a interface overlay to the one or more non-transitory electronic storage devices comprising, the formulary, thereby creating, following receipt, further member-specific modifications to the existing data of the formulary such that the PBM system is configured to cause automatic generation of a standardized code indicating denial of coverage due to available and unperformed genetic testing ("genetic testing availability code") for the queried medication upon subsequent querying, in responses to receiving further ones of the standardized requests for coverage information, the formulary for the billing information for the medications indicated in the modified data as being available for yet unperformed genetic testing for the members;

receiving, at the PBM system from a pharmacy system or the EHR system, the standardized requests for coverage information, said standardized request each including a standardized code identifying a respective one of the medications;

querying, by way of the PBM system, for each of, based on, and in response to receipt of, the standardized requests, the one or more non-transitory electronic storage devices comprising the formulary associated with the PBM system for billing information for the medications and the members, said formulary comprising data regarding prescription drugs covered by a prescription drug plan or plans for the members, associated billing information, and the member-specific modifications to the data indicating certain of the prescription drugs contraindicated for at least certain of the members, including e-member, based member specific genetic testing results data for such members; and for at least one standardized requests:

receiving, at the pharmacy system by way of the PBM system and in response to querying the formulary associated with the PBM system based on and in response to the standardized request, a standardized communication including the genetic contraindication code indicating that dispensing of the medication for the member as indicted in the standardized request is not authorized for the member based on the genetic testing results data for the member indicating that the medication is wholly or partially ineffective for the member;

in response to receiving the genetic contraindication code, further querying an alternative treatment database for an alternative medication for the medication;

in response to receiving the alternative medication, transmitting, by way of a modification platform interposed between, separate from, and in electronic communication with the PBM system and the EHR system for the member, a standardized change request to the EHR system for the member for approval by a healthcare provider for the member requesting change from the medication to the alternative medication, including a standardized code identifying the alternative medication; and receiving, in response to receiving the change request, a standardized communication indicating approval of the change request at the modification platform from the EHR system for the member at the medication platform, and in response, causing the patient data at the EHR system for the member to be updated to reflect prescription of the alternative medication instead of the medication, and transmitting a standardized communication to the PBM system including the standardized code for the alternative medication indicating approved prescription of the alternative medication in substitution for the medication.

2. The method of claim 1 further comprising the steps of:

initiating, at a health plan system associated with the PBM, an electronic review of the modified data to identify a subset of the members for which the genetic testing availability code would be generated;

electronically generating and transmitting a standardized communication to the identified subset of members requesting electronic consent for the genetic testing ("consent communication");

in response to receiving the consent for testing from consenting ones of the identified subset of members ("consenting members") in response to the consent communication, providing a standardized testing request communication to the LIS including requested genetic testing and mailing information for the consenting members;

in response to receiving the standardized testing request communication, and by way of one or more robots under operative control of the LIS, generating a testing kit for each of the consenting members comprising a genetic material gathering device, instructions, and a return label; and performing genetic testing on received specimens at the one or more genetic sequencing machines from returned ones of the genetic material gathering devices in accordance with the ordered genetic testing.

3. The method of claim 1 further comprising:

generating, by way of the PBM system and in response to receiving the genetic contraindication code, standardized report data for the medication comprising a PGx contraindication indicator; and transmit, by way of the PBM system, the standardized report data to an originating one of the pharmacy system and the EHR system for the standardized request for coverage.

4. The method of claim 3 wherein:

the standardized report data, upon access for display at an electronic display of the originating one of the pharmacy system and the EHR system, is configured to generate a table comprising a medication name column, a therapeutic class column, a dose/strength column, a status information column comprising the billing information, and a notes and restrictions column; and the PGx contraindication indicator comprises an icon or graphic provided at the notes and restrictions column.

5. The method of claim 1 wherein:

each of the standardized codes comprises a National Council for Prescription Drug Programs ("NCPDP") accepted code.

6. The method of claim 1 wherein:

at least the standardized request for coverage information, the standardized communication including the genetic contraindication code, the standardized change request, and the standardized communication indicating approval of the change request comprise HL7 communications.

7. One or more non-transitory electronic storage devices comprising software instructions, which when executed, configure one or more processors to:

carry out the method of claim 1.

8. A system for alerting, at the point of prescribing or prescription fulfillment, using interoperable, standardized messaging, to wholly or partially ineffective medications for a member based on the member's relevant genetic makeup and updating electronic medical records data comprising patient data stored at an electronic health record ("EHR") system for the member, said system comprising:

the EHR system associated with a healthcare provider for the member and comprising the patient data for the member, including prescribed medications and diagnosed diseases;

a modification platform, separate from and in electronic communication with, the EHR system and a pharmacy benefits manager ("PBM") system;

a pharmacy system configured to receive electronic prescription requests from the healthcare provider by way of the EHR system; and the PBM system associated with a health plan and in electronic communication with the pharmacy system comprising or associated with one or more processors and one or more non-transitory electronic storage devices comprising a formulary comprising data regarding prescription drugs covered by a prescription drug plan or plans for members, including the member, associated billing information, and associated clinical information including member-specific modifications to the data indicating certain of the prescription drugs contraindicated for the respective member based genetic testing results data for the respective member and alternative treatment options, said one or more non-transitory electronic storage devices comprising executable software instructions, which when executed, configure said one or more processors to, electronically and automatically:

receive, from the pharmacy system or the EHR system, a standardized request for coverage information regarding a medication for the member prescribed by the healthcare provider by way of the EHR system, said standardized request including a first standardized code identifying the medication;

query, based on and in response to receipt of the standardized request, the formulary for the billing information associated with the medication and the member;

where the query indicates that the medication is genetically contraindicated for the member, generate a second standardized code indicating that dispensing of the medication is not authorized for the member based on the genetic testing results data for the member indicating that the medication is wholly or partially ineffective for the member ("genetic contraindication code"); and where the genetic contraindication code is generated, further query the alternative treatment options for an alternative medication for the medication, transmit, by way of the modification platform, a standardized change request to the EHR system for the member for approval by the healthcare provider comprising the second standardized code and a third standardized code identifying the alternative medication, and where approval of the change request is received from the EHR system by way of the modification platform, cause the EHR system to be automatically updated to reflect prescription of the alternative medication instead of the medication within the member data; and a laboratory information system ("LIS") associated with a laboratory and one or more genetic sequencing machines, said LIS having operative control over said one more genetic sequencing machines and comprising one or more processors and one or more non-transitory electronic storage devices comprising executable software instructions, which when executed, configure said one or more processors to, automatically and electronically:

cause the one or more genetic sequencing machines to carry out genetic testing;

receive the genetic testing results data from the one or more genetic sequencing machines;

automatically generating a data interface overlay reflecting the genetic test results data configured to create the member-specific modification to existing data of the formulary upon application thereto;

transmit the data interface overlay to the one or more non-transitory electronic storage devices comprising the formulary for integration therewith, thereby causing, following receipt, the member-specific modifications to the existing data of the formulary such that such that the PBM system is configured to cause automatic generation of the second standardized code upon subsequent querying in re es to receiving further ones of the standardized request for coverage information for members and medications indicated in the modified data as being known to be partially or wholly ineffective in persons having a same relevant genetic makeup as the members according to the genetic testing results data;

generate a second data interface overlay including available, but unperformed, genetic testing for medications, including the medication; and transmit the second data interface overlay to the one or more non-transitory electronic storage devices comprising the formulary, thereby creating, following receipt, further member-specific modifications to the existing data of the formulary such that the PBM system is configured to cause automatic generation of a fourth, standardized code indicating denial of coverage due to available and unperformed genetic testing for the medication upon subsequent querying in responses to receiving further ones of the standardized request for coverage information for medications and members indicated in the modified data as being available for yet unperformed genetic testing.

9. The system of claim 8 further comprising:

a health plan system for the member and other members in electronic communication with the PBM system and comprising a review module and a notification module, wherein said review module is configured to, automatically and electronically, review the formulary for said member and said other members to identify a subset of members for which genetic testing is available in accordance with the modified data and one or more criteria defined by a health plan, and wherein said notification module is configured to generate and transmit a standardized communication to each of the identified members requesting electronic consent for the genetic testing, and transmit, in response to receipt of indication of electronic consent for the genetic testing from one or more of the contacted members ("consenting members"), requested genetic testing and mailing information regarding the consenting members to the LIS.

10. The system of claim 9 further comprising:

a test kit assembly subsystem comprising associated with the laboratory and under operative control of the LIS, said test kit assembly subsystem configured to generate test kits the consenting members in an at least partially automated fashion, wherein said test kits comprise genetic material gathering devices, instructions, and labels printed with the mailing information for the consenting members.

11. The system of claim 10 further comprising:

an automated testing subsystem associated with the laboratory and under operative control of the LIS and comprising the one or more genetic sequencing machines, said automated testing subsystem configured to:

assemble testing devices for PGx testing for each specimen returned to the laboratory from the genetic material gathering devices from the test kits in an at least partially automated fashion;

perform PGx testing on the specimens at the one or more genetic sequencing machines in an at least partially automated fashion; and electronically report the genetic testing results data from the one or more genetic sequencing machines to the LIS.

12. The system of claim 11 wherein:

said test kit assembly subsystem and said automated test subsystem comprise one or more controllers, handling robots, conveyor systems, and printers under operative control of the LIS.

13. The system of claim 8 wherein:

the one or more non-transitory electronic storage devices of the PBM system comprise additional executable software instructions, which when executed, configure said one or more processors of the PBM system to, electronically and automatically:

generating, in response to receiving the second standardized code, standardized report data for the medication comprising a PGx contraindication indicator; and transmit, by way of the PBM system, the standardized report data to the pharmacy system, wherein the standardized report data, upon access for display at an electronic display of the originating one of the pharmacy system and the EHR system, is configured to generate a table comprising a medication brand name column, a therapeutic class column, a dose/strength column, a status information column comprising the billing information, and a notes and restrictions column, where the PGx contraindication indicator comprises an icon or graphic provided at the notes and restrictions column.

14. The system of claim 8 wherein:

at least the standardized request for coverage information and the standardized change request comprise HL7 communications.

15. The system of claim 8 wherein:

each of the first, second, third, standardized codes comprises a respective National Council for Prescription Drug Programs ("NCPDP") accepted code.

16. A method for automatically alerting, at the point of prescribing or prescription fulfilment, using interoperable, standardized messaging, to wholly or partially ineffective medications for a member based on the member's relevant genetic makeup, said method comprising the steps of, electronically and automatically:

causing performance of genetic testing on genetic material samples by one or more genetic sequencing machines for one or more individuals to generate genetic testing results data;

generating a data interface overlay including the genetic testing results data and configured to create member-specific modifications to existing data of a formulary upon application thereto, said formulary comprising data regarding prescription drugs covered by a prescription drug plan or plans for members and associated billing information;

applying the data interface overlay to one or more non-transitory electronic storage devices comprising the formulary for integration therewith, thereby creating, following receipt, the member-specific modifications to existing data of the formulary such that standardized codes are automatically generated upon subsequent query of the formulary for the billing information in responses to receiving standardized requests for coverage information for members and medications indicated in the modified data as being known to be partially or wholly ineffective in persons having a same relevant genetic makeup as the members according to the genetic testing results data ("genetic contraindication code");

generating a second data interface overlay including available, but unperformed, genetic testing for medications; and applying the second data interface overlay to the one or more non-transitory electronic storage devices comprising the formulary, thereby creating, following receipt, further member-specific modifications to the existing data of the formulary such that a standardized code indicating denial of coverage due to available and unperformed genetic testing ("genetic testing availability code") is automatically generated upon subsequent querying of the formulary for the billing information in responses to receiving further ones of the standardized requests for coverage information, for the members, for any medications indicated in the modified data as being available for yet unperformed genetic testing for the members.

17. The method of claim 16 further comprising:

receiving, at a pharmacy benefits manager ("PBM") system, the standardized requests for coverage information regarding medications prescribed by healthcare providers for the members;

querying, by way of the PBM system and based on and in response to receipt of the respective standardized requests, the one or more non-transitory electronic storage devices comprising the formulary associated with the PBM system for the billing information for the medications and the members, said formulary comprising the member-specific modifications to the data from the data interface overlay and the second data interface overlay;

receiving, in response to querying the formulary based on and in response to at least one of the standardized requests, a standardized communication including the genetic contraindication code; and receiving, in response to querying the formulary based on and in response to at least other one of the standardized requests, a second standardized communication including the genetic testing availability code.

* * * * *